(12) United States Patent
Zeng et al.

(10) Patent No.: US 9,804,092 B2
(45) Date of Patent: Oct. 31, 2017

(54) INTEGRATED SPECTRAL PROBE FOR RAMAN, REFLECTANCE AND FLUORESCENCE SPECTRAL MEASUREMENTS

(71) Applicant: British Columbia Cancer Agency Branch, Vancouver (CA)

(72) Inventors: Haishan Zeng, Vancouver (CA); Michael Short, Coquitlam (CA); Jianhua Zhao, Langley (CA)

( * ) Notice: Subject to any disclaimer, the term of this patent is extended or adjusted under 35 U.S.C. 154(b) by 0 days.

(21) Appl. No.: 14/766,451

(22) PCT Filed: Feb. 11, 2014

(86) PCT No.: PCT/CA2014/050093
§ 371 (c)(1),
(2) Date: Aug. 6, 2015

(87) PCT Pub. No.: WO2014/124531
PCT Pub. Date: Aug. 21, 2014

(65) Prior Publication Data
US 2015/0377787 A1   Dec. 31, 2015

Related U.S. Application Data

(60) Provisional application No. 61/764,899, filed on Feb. 14, 2013.

(51) Int. Cl.
*G01N 21/65* (2006.01)
*G01N 21/64* (2006.01)
*G01J 3/44* (2006.01)
*A61B 5/00* (2006.01)
*G01J 3/02* (2006.01)

(52) U.S. Cl.
CPC .......... *G01N 21/65* (2013.01); *A61B 5/0071* (2013.01); *A61B 5/0075* (2013.01);
(Continued)

(58) Field of Classification Search
CPC ..................................................... G01J 3/0221
See application file for complete search history.

(56) References Cited

U.S. PATENT DOCUMENTS

| | | | | |
|---|---|---|---|---|
| 6,069,689 A | * | 5/2000 | Zeng | A61B 5/0059 356/301 |
| 2004/0162489 A1 | * | 8/2004 | Richards-Kortum | A61B 5/0071 600/473 |

(Continued)

OTHER PUBLICATIONS

Short, Michael A., et al. "Using laser Raman spectroscopy to reduce false positives of autofluorescence bronchoscopies: a pilot study." Journal of Thoracic Oncology 6.7 (2011): 1206-1214.*
(Continued)

*Primary Examiner* — Shawn Decenzo (57) ABSTRACT

Examples of a spectroscopy probe for performing measurements of Raman spectra, reflectance spectra and fluorescence spectra are disclosed. The integrated spectral probe can comprise one or more light sources to provide a white light illumination to generate reflectance spectra, an excitation light to generate an UV/visible fluorescence spectra and a narrow band NIR excitation to induce Raman spectra. The multiple modalities of spectral measurements can be performed within 2 seconds or less. Examples of methods of operating the integrated spectroscopy probe disclosed.

16 Claims, 7 Drawing Sheets

(52) U.S. Cl.
CPC ......... *A61B 5/0084* (2013.01); *G01J 3/0221* (2013.01); *G01J 3/4406* (2013.01); *G01N 21/64* (2013.01); *G01N 21/645* (2013.01); *A61B 5/0086* (2013.01); *A61B 2560/0285* (2013.01); *G01J 3/0213* (2013.01); *G01N 2021/6417* (2013.01); *G01N 2021/6484* (2013.01); *G01N 2201/08* (2013.01); *G01N 2201/084* (2013.01); *G01N 2201/0833* (2013.01)

(56) References Cited

U.S. PATENT DOCUMENTS

| | | | | |
|---|---|---|---|---|
| 2007/0095180 A1* | 5/2007 | Zhang | ............... | B26D 3/06 83/13 |
| 2007/0167836 A1* | 7/2007 | Scepanovic | ......... | A61B 5/0071 600/476 |
| 2009/0270702 A1* | 10/2009 | Zeng | ............... | A61B 5/0075 600/323 |

OTHER PUBLICATIONS

Pawluk, Hanna C., et al. "Improvements to a laser Raman spectroscopy system for reducing the false positives of autofluorescence bronchoscopies." SPIE BiOS. International Society for Optics and Photonics, 2012.*

Short, Michael A., et al. "Development and preliminary results of an endoscopic Raman probe for potential in vivo diagnosis of lung cancers." Optics letters 33.7 (2008): 711-713.*

* cited by examiner

INTEGRATED SPECTRAL PROBE FOR RAMAN, REFLECTANCE AND FLUORESCENCE SPECTRAL MEASUREMENTS

TECHNICAL FIELD

The present invention relates generally to an integrated spectral probe that facilitates integrated measurements of Raman spectra, reflectance spectra and fluorescence spectra.

BACKGROUND

Generally speaking, the measurement of reflectance or fluorescence or Raman signals plays a great role in biomedical applications, for example for the early diagnosis of disease-specific changes on the molecular level.

Reflectance spectroscopy is an analysis of a light reflected from tissue. Tissue reflectance spectroscopy can be used to derive information about molecules that absorbs light strongly, e.g. tissue chromophores. It can also be used to derive information about tissue scatterers, such as the size distribution of cell nucleus and average cell density.

Fluorescence spectroscopy is the analysis of fluorescence emission from tissue. Native tissue fluorophores (molecules that emit fluorescence when excited by appropriate wavelengths of light) can be sensitive to chemical composition and chemical environment changes associated with disease transformation.

Raman spectra convey specific information about the vibrational, stretching, and breathing bond energies of an illuminated sample. Raman spectroscopy probes molecular vibrations and gives very specific, fingerprint-like spectral features and has high accuracy for differentiation of malignant tissues from benign tissues. Raman spectroscopy can also be used to identify the structural and compositional differences on proteins and genetic materials between malignant tissues, their pre-cursers, and normal tissues. Naturally the Raman signal is very weak comparable to the reflectance or the fluorescence signal. In addition, the weak Raman signal can be further impeded by the interference from tissue fluorescence, and spectral contamination caused by the background Raman and fluorescence signals generated in fibers transmitting illumination light and/or spectral signals.

SUMMARY

In one aspect, an integrated spectroscopy system is provided. The integrated spectroscopy system probe facilitates integrated measurements of Raman spectra, reflectance spectra and fluorescence spectra. The integrated spectroscopy system comprises a light source, a spectroscopy probe coupled to the light source, a first detector and at least one additional detector. The light source is configured to provide a white light illumination beam to generate reflectance spectra, an excitation light beam to generate an UV/visible fluorescence spectra and a narrow band excitation light beam to induce Raman spectra and infrared fluorescence spectra. The spectroscopy probe comprises at least one narrow band excitation fiber configured to transmit the narrow band excitation light beam to a target, at least one white light illumination fiber configured to transmit the white light illumination beam to the target, at least one excitation illumination fiber configured to transmit the excitation light beam to the target, a plurality of Raman collection fibers configured to collect a returning radiation reflected and emitted from the target in response to the narrow band excitation light beam, at least one reflectance collection fiber configured to collect a returning radiation reflected from the target in response to the white light illumination beam, and at least one fluorescence collection fiber configured to collect returned radiation emitted from the target in response to the excitation light beam. The first detector is coupled to the plurality of Raman collection fibers to detect a Raman spectrum. The at least one additional detector is coupled to the at least one reflectance collection fibers and/or the at least one fluorescence collection fibers to detect a reflectance spectrum and/or a fluorescence spectrum.

In one aspect, pluralities of spectral measurements are being performed within 2 seconds or less.

In another aspect, the integrated spectroscopy system comprises an optical modulator mounted in front of the light source to modulate the illumination light to provide the white light illumination light beam, the excitation light beam and the narrow band excitation beam. The optical modulator comprises a first filter configured to pass visible light below 750 nm, a second filter configured to pass excitation light in a blue wavelength range and a third filter configured to pass light in a 785±20 nm wavelength range.

In one aspect, the light source comprises a monochromatic light source configured to provide the narrow band excitation light beam, a broadband light source configured to provide white light illumination light beam and a excitation light source configured to provide the excitation light beam. The monochromatic light source is coupled to the at least one narrow band excitation fiber, the broadband light source is coupled to the at least one white light illumination fiber and the excitation light source is coupled to the at least one excitation illumination fiber.

In one aspect, the broadband light source and the excitation light source are integrated into one light source. The integrated light source provides a white light illumination light beam and the excitation light beam sequentially.

In another aspect, the at least one narrow band excitation fiber is spaced apart from the plurality of Raman collection fibers, the at least one white light illumination fiber is spaced apart from the at least one reflectance collection fiber, and the at least one excitation illumination fiber is spaced apart from the at least one fluorescence collection fiber.

In one aspect, the integrated spectroscopy system further comprises a filter assembly mounted at a distal end of the spectroscopy probe. The filter assembly comprises a short pass filter placed over the at least one narrow band excitation fiber to pass light in a 785±5 nm wavelength range and a long pass filter placed over the plurality of Raman collection fibers to block light in a 785 nm wavelength range and pass light in a wavelength range above 800 nm.

In another aspect, the integrated spectroscopy system further comprises a control system that is in optical communication with the light source to control the output illumination of the light source. The control system is further in optical communication with the first detector and at least one additional detector to control the operation of the first detector and at least one additional detector.

In one aspect, the light source provides simultaneously the white light illumination beam and the narrow band excitation beam such that the first detector and the one additional detector provide simultaneously the Raman spectrum and the reflectance spectrum.

In another aspect, the light source provides simultaneously the excitation light beam and the narrow band excitation light beam such that the first detector and the one additional detector provide simultaneously the Raman spectrum and the fluorescence spectrum.

In yet another aspect, the light source provides the narrow band illumination light beam to generate simultaneously a Raman spectrum and an infrared fluorescence spectrum such that the first detector can provide simultaneously the Raman spectrum and the infrared fluorescence spectrum.

In another aspect, a method for taking integrated measurements of Raman spectra, reflectance spectra and fluorescence spectra is provided.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

DETAILED DESCRIPTION OF SPECIFIC EMBODIMENTS

For successful in vivo Raman spectral measurement a Raman system needs to incorporate a filtering mechanism configured to minimize or eliminate background Raman and fluorescence signals generated from the fiber-optic material and to be able to collect enough signal so that a Raman spectrum can be acquired in seconds or sub-seconds.

Figure 1:
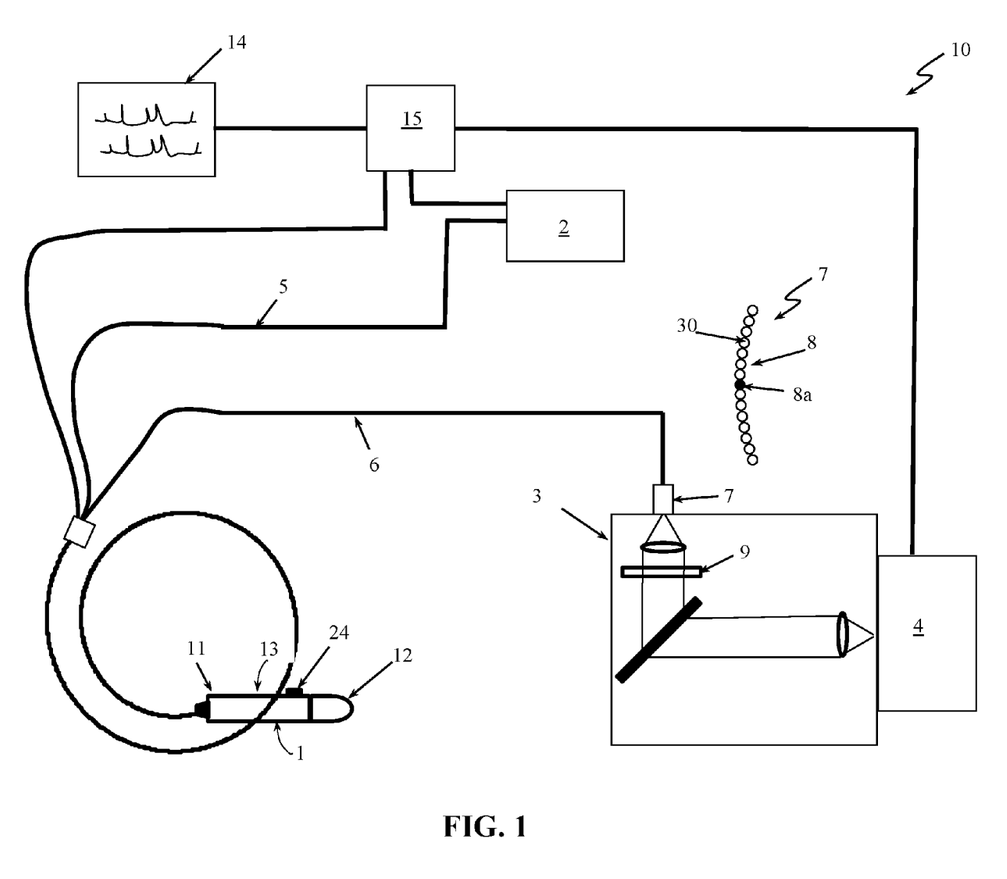
FIG. 1 is a block diagram of an example of a Raman spectral system.
Figure 2:
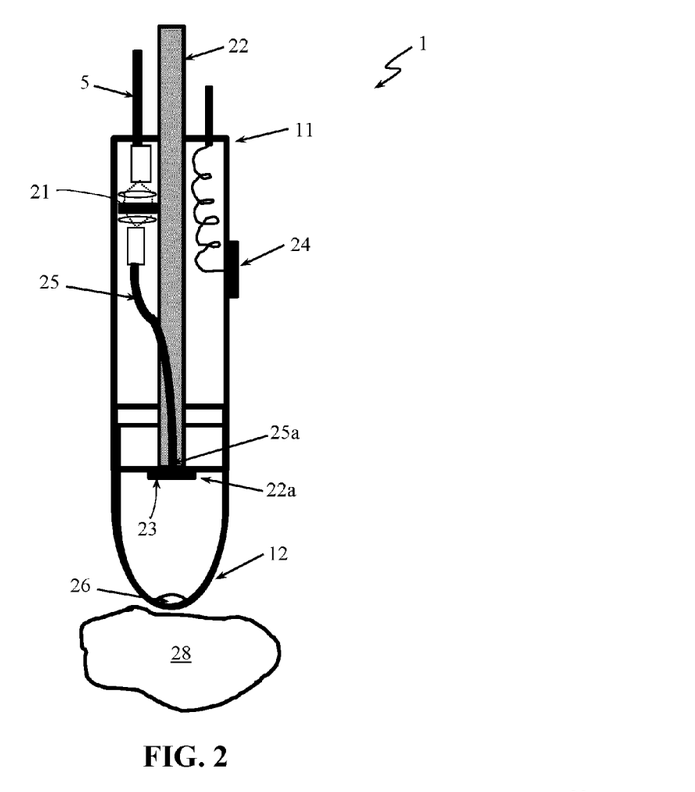
FIG. 2 is a cross-sectional view of an example of a Raman spectral probe.

FIG. 1 schematically shows an example of a Raman system 10. The Raman system 10 can comprise a probe 1, a light source 2, a spectrograph 3 and a detector 4. The light source 2 can be a monochromatic light source such as a laser which can provide excitation light capable of inducing Raman scattering in a subject, such as for example a tissue 28 (FIG. 2). Any other light source or combinations of light sources can be used that can provided excitation light to induce Raman scattering in the subject illuminated by the excitation light. The light source 2 can be configured to minimize the interference from non-desired sources, e.g., the light source can be selected to minimize the fluorescence from the tissue and the absorption of photons emanating from melanin. The light source 2 can be optically coupled to a proximal end of an illumination light transmission guide 5. The illumination light from the light source 2 can be focused into the illumination light guide 5. The illumination light can be a laser light at 785 nm. Other wavelengths can be chosen depending on the properties of the molecules of interest. For example, a light source that produces a longer wavelength light than the 785 nm wavelength can be used, e.g. the light source that produces 1064 nm light can be used so that the strong fluorescence background of the tissue can be avoid. A distal end of the illumination light guide 5 can be connected to the probe 1 at its proximal end 11. The probe 1 can be designed to maximize collection of tissue Raman signals while reducing the interference of Rayleigh scattered light, fiber fluorescence and Raman background signals. The probe 1 can be a hand-held probe and can comprise the proximal end 11, a distal end 12 and an elongated body 13. In some implementations, the probe 1 can be an endoscopy probe.

FIG. 2 shows the probe 1 in details. The illumination light guide 5 entering the probe 1 can be connected to a filter 21 located inside the probe 1. The filter 21 can be a laser line filter that can pass 785 nm illumination light while blocking any other wavelengths. Any other type of band-pass filter that can pass the desired excitation light and can filter out background Raman and fluorescence signals generated inside the illumination guide 5 between the light source 2 and the filter 21 can be used without departing from the scope of the invention. The filtered light can be refocused into the illumination fiber 25 in a probing fiber bundle assembly 22. Because this part (illumination fiber 25) of the illumination light guide is short, the generated background Raman and fluorescence from the fiber can be small. At a distal end 22a the probing fiber bundle assembly 22 is coated with a filter assembly 23, shown in details in FIGS. 2A and 2B. An induced Raman signal from the subject (i.e. tissue 28) can be collected by a plurality of collection fibers 30. In one implementation of the probing fiber bundle assembly 22, the collection fibers 30 can be arranged around the illumination fiber 25. The probe 1 can further comprise a trigger button or switch 24 that can be electrically connected to a controller 15 (FIG. 1). The trigger button or switch 24 can trigger the light source 2 to generate the excitation illumination light and/or to trigger the spectrograph 3 and the detector 4 to take Raman measurements.

Figure 2A:
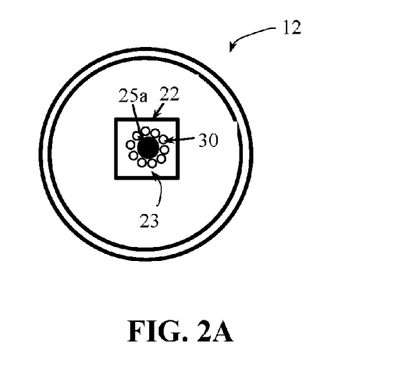
FIG. 2A is a top view of a distal end of a probing fiber bundle assembly showing a short-pass filter coating over an excitation illumination fiber and a long-pass filter coating over collection fibers.
Figure 2B:
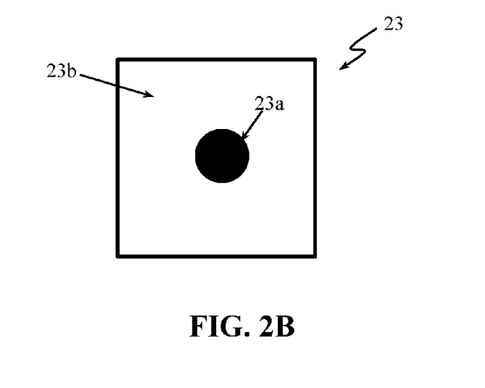
FIG. 2B is a top view of a filter assembly showing a filter substrate with a short-pass filter coating and a long-pass filter coating.

FIG. 2A is a top view of the distal end 12 of the probe 1 showing the fiber bundle 22 and filter assembly 23. FIG. 2B shows in details the filter assembly 23. The filter assembly 23 can comprise a short-pass filter 23a coated over a distal end 25a of the illumination fiber 25 to further reduce the background signals. For example, the short-pass filter can pass 785 nm excitation light while can block light above 810 nm (810 nm-1000 nm). The filter assembly 23 can further comprise a long-pass filter coating 23b that can be applied to distal ends of collection fibers 30 to block the backscattered laser light from entering the probe 1. For example, the long pass filter 23b can pass light of 815 nm to 1000 nm but can block the 785 nm laser light.

Figure 3:
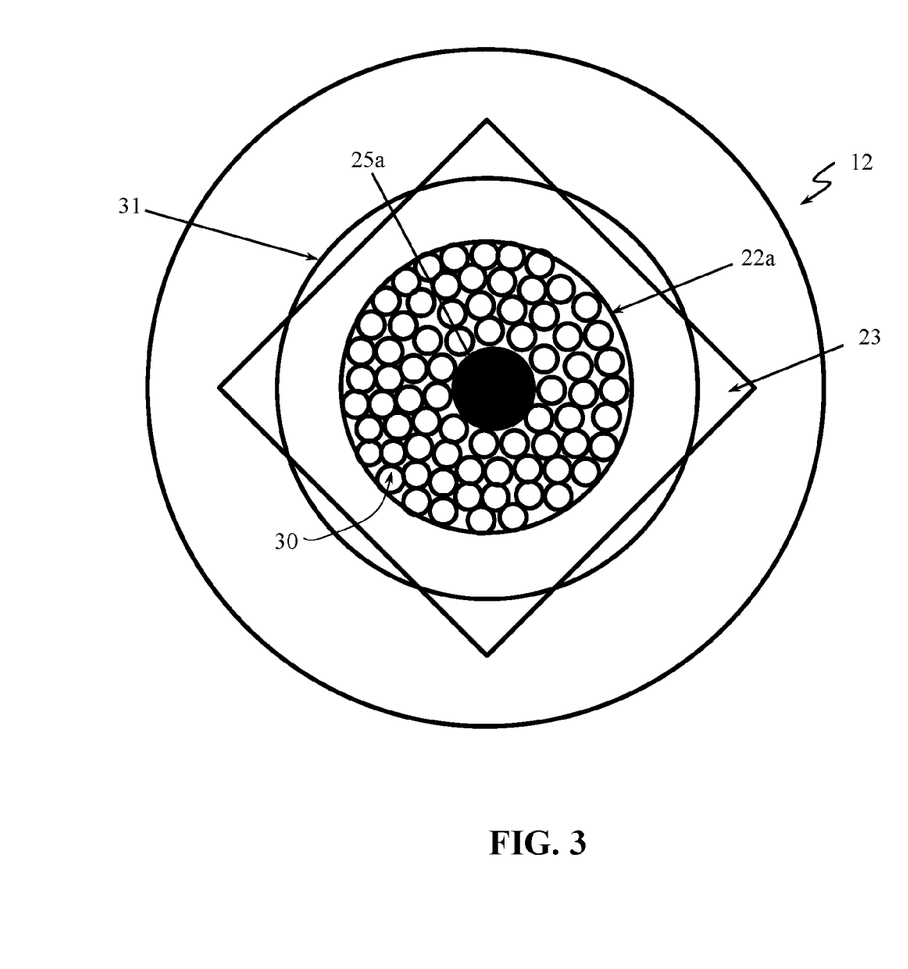
FIG. 3 is a top view of a distal end of a probing fiber bundle assembly coated with a filter assembly.

FIG. 3 shows the distal end 12 of the probe 1 showing the distal end 22a of the probing fiber bundle assembly coated with a filter assembly 23. At the example illustrated in the FIG. 3, at a distal common end 22a of the probing fiber bundle assembly, the illumination fiber 25 can be located at a center of the bundle assembly and its end 25a can be coated with the short-pass filter 23a. The collection fibers 30 can be arranged around the illumination fiber 25 and their ends can be coated with the long-pass filter 23b. In one implementation, the filter coatings 23a, 23b can be evaporated directly onto the respective fibers. In another implementation the respective filter coatings 23a, 23b can be evaporated onto a substrate to form for example, a patterned filter that can be glued to the distal end 22a of the probing fiber bundle assembly 22. The substrate can be dimensioned to be as thin as possible. The part of the filter assembly 23 consisting of the short pass filter 23a can be aligned to cover the excitation illumination fiber 25 while the part of the filter assembly 23 consisting of the long pass filter 23b can be aligned to cover the collection fibers 30. A grooved channel 31 can be formed at the distal end 22a of the probing fiber bundle assembly 22, dimensioned as glue run off channel, to prevent the glue from the filter substrate to flow over to the fibers. If the glue reaches the fibers 25, 30 it can generate interfering Raman and fluorescence signals. The channel 31 can have circular shape formed around the filter assembly 23 or any other suitable shape.

As shown in FIG. 2, at the proximal end 11 of the probe 1 the probing fiber bundle assembly 22 can branch out into the single illumination fiber 5 and a collection fiber bundle 22 arranged to form the detection fiber guide 6 (see FIG. 1). In one embodiment, the detection guide 6 can have geometrical shape such as a circle, a square, a rectangle or a hexagon, at the proximal end 11 of the probe 1. The shape can be other than filled-in if desired.

In one implementation, the illumination fiber 25 can be metal coated (e.g. gold coated) for optical isolation to prevent cross-talks with the collection fibers 30. In one implementation, the illumination guide 25 and/or each of the collection fibers 30 can comprise an anti-reflection coating to prevent cross-talking between the fibers. The probe 1 can further comprise an opening 26 located at the distal end 12 of the probe 1 to keep the probe 1 at a fixed distance from the tissue surface. Inside surfaces of the probe 1 can be coated in black to prevent reflection of the light. In addition, the inside of the probe 1 should be coated with a material that does not generate Raman signals when the back-scattered Raman excitation light from the tissue 28 is incident inside the distal end 12. The distal end 12 can be made of a metal or a plastic material. In one implementation, only the distal end 12 of the probe 1 can be coated in black and with a material that does not generate Raman signals. In one embodiment the distal end 12 can be disposable after completion of the measurements to prevent cross-contamination between patients. In one implementation, the opening 26 can be a quartz window or any other material with low Raman and fluorescence background.

To achieve a high signal to noise ratio in the performance of the Raman system 10 the probing fiber bundle assembly 22 can accommodate about fifty (50) to hundred fifty (150) collection fibers 30 of 100 µm core diameter and a 200 µm illumination fiber 25. The fibers 25, 30 can be low-OH fused silica type with numerical aperture of about 0.22. In one mode of operation, the light source 2 can produce a 785 nm excitation spot with size of about 3.5 mm in diameter. This excitation light can induce Raman scattering in the illuminated subject. The collection fibers 30 can be configured to collect the scatter light in 1 second or less in order to form a spectrum with high signal to noise ratio. At the proximal end 11 of the probing fiber bundle assembly 22, the collection fibers 30 can be packed closely into a round fiber bundle to form the detection guide 6. For example, the diameter of the detection guide 6 at the proximal end 11 of the probe 1 can be about 1-2 mm. The detection guide 6 can be connected to a linear fiber adapter 7 (see FIG. 1) at an entrance to the spectrograph 3. The linear fiber adapter 7 can comprise a round-to-parabolic linear array fiber bundle, such as a parabolic arc 8. So, at the entrance of the spectrograph 3, the collection fibers 30 can be aligned along a parabolic line to correct for image aberration of the spectrograph 3 to achieve better spectral resolution and a higher signal to noise ratio. The collection fibers 30 of the detection guide 6 can be aligned along a curved line formed by laser drilling of a stainless steel cylinder piece. The linear fiber adapter 7 can accommodate as many of the 100 µm core collection fibers 30 as possible in a 13 mm arc length allowing for a small gap between each fiber so that the lined fibers 30 can simulate a slit of about 13 mm high that can be imaged onto the detector 4. In the middle of the parabolic arc can be positioned a calibration fiber 8a and the collection fibers 30 can be symmetrically arranged above and under the calibration fiber 8a. The linear adapter can have a numerical aperture of 0.22 to match a numerical aperture of the spectrograph 3 for achieving best coupling efficiency.

The spectrograph 3 can further comprise a filter 9 to select the Raman bands of interest and to further ensure that no laser light can proceed into the detector 4. For example, the filter 9 can be a long pass filter that can pass light in the 815 nm-1000 nm wavebands but can block a 785 nm laser line. The filtered signal is directed onto the detector 4. The detector 4 can be pixelated detector, such as a charge coupled device (CCD), a charge injection device (CID), an intensified CCD detector, a photomultiplier tube (PMT) detector array, a photo-diode array (PDA), an intensified PDA, etc. The signal from the detector 4 can be directed to the controller 15 and a processing unit 14. The controller 15 that can be adapted and configured to control the light source 2, to turn the light source 2 on and off as well as to control the output power of the light source 2. Alternatively, the light source 2 can be self-powered and only controlled through controller 15 using a wired interface or a wireless interface. The controller 15 can further be adapted and configured to control the power to the detector 4 and the spectrograph 3 to turn the detector 4 on and off and to read the Raman spectra data as well as to receive the spectra data signals from the detector 4. The controller 15 can receive Raman spectra data from the detector 4 and forward it to the processing unit 14 for further processing and analysis. In addition, the controller 15 can receive control signals from the processing unit 14 to control the operation of the light source 2, the spectrograph 3 and/or the detector 4. In addition, the controller 15 can be connected to the trigger button or switch 24 to enable the spectrograph 3 and the detector 4 to take the Raman spectra reading upon the pressing or depressing of the trigger button or switch 24.

In one implementation, the controller 15 can be configured to send a signal to an ambient light source (not shown) to automatically turn off the ambient light. For example the ambient light can be switched off for a predetermined time, e.g. one or two seconds. In one example, once the trigger switch 24 is turned on, it can send a signal to the controller 15 to switch off the ambient light. Once the detector 4 detects the measured signal, it can send a signal to the controller 15 to turn on the ambient light. This can actually provide a way to tell the operator that the measurements have been completed. In one embodiment, the controller 15 can send a signal to a monitor, which can be part of the processing unit 14, to automatically turn off the monitor during the spectral measurements and to turn it on once the spectral measurements have been completed.

Figure 4:
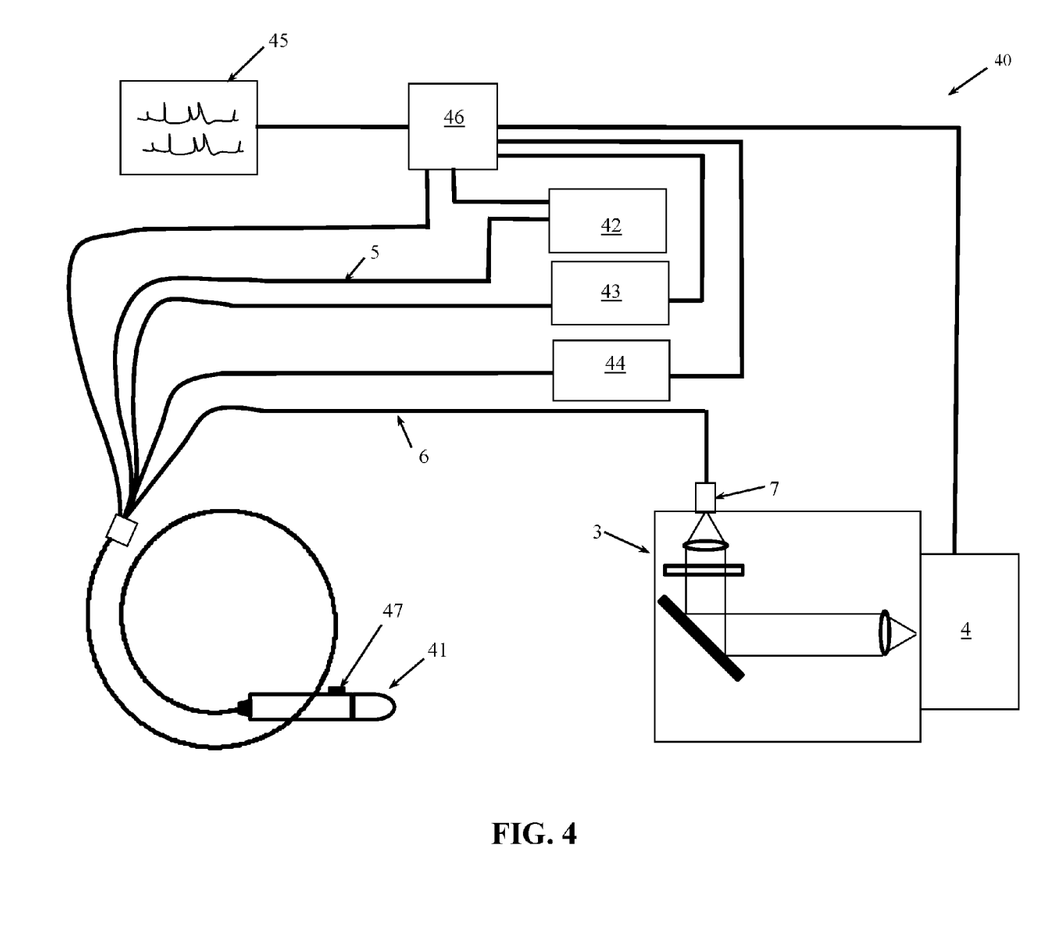
FIG. 4 is a block diagram of an example of an integrated spectroscopy system for measuring Raman spectra, reflectance spectra and fluorescence spectra.

FIG. 4 schematically illustrates an integrated spectroscopy system 40 for facilitating Raman spectroscopy, reflectance spectroscopy and fluorescence spectroscopy. The integrated spectroscopy system 40 can comprise a hand-held spectroscopy probe 41, a monochromatic light source 42, a white and blue light illumination source 43, a spectrometer 44, a spectrograph 3, a detector 4, a controller 46 and a processing unit 45. The monochromatic light source 42 can be a laser and can provide an excitation light capable of inducing Raman scattering in the illuminated subject similarly to the Raman system 10 of FIG. 1. The excitation light generated by the light source 42 and filtered out through the filter 21 as described herein above in relation with the system 10 of FIG. 1 is directed to the subject under examination using the light guide 5 and illumination fiber 25 (see FIGS. 1-3). The light source 43 can produce a broadband illumination such as a white light illumination light for reflectance spectra measurements and an excitation illumination light for fluorescence spectral measurements. The light sources 43 can be a single unit or can be comprised of a combination of light sources to deliver the desired illumination. One or more LEDs can provide illumination for producing the white light illumination and the fluorescence excitation light. These light sources can be electronically switched at high rates to provide the two modality illuminations. In one embodiment, the light source 43 can be a single unit that can produce a white light illumination light and blue excitation light.

In one implementation, the light sources 42 and 43 can be a single unit that can produce a broad band illumination light that can then interacts with an optical modulator, such as for example a rotating filter wheel that can consists of a plurality of filters to provide a plurality of output illumination light such as a white light illumination for reflectance measurements, a blue excitation light for fluorescence measurements, and a near infrared (NIR) excitation for Raman measurements and/or NIR fluorescence measurements.

The modulated illumination light beams are transmitted to the probe 41 and are directed to the targeted subject. The modulated illumination light beams can interact with the target which in response to each of the modulated illumination light beams can produce a respective reflectance spectral signal, a fluorescence spectral signal, a Raman spectral signal or a NIR fluorescence spectral signal. The Raman spectra can then be collected by the collection fibers 30 and through the detection guide 6 can be directed to the linear fiber adapter 7, the spectrograph 3 and the detector 4. The reflectance spectra and the fluorescence spectra can be directed to a respective spectrometer, such as the spectrometer 44. The spectrometer 44 can be a single spectrometer configured to detect both the reflectance and the fluorescence spectra or can be two separate spectrometers. For example, the spectrometer 44 can be a compact spectrometer and can be configured to detect both reflectance spectra and fluorescence spectra. The signals from the detector 4 and/or the spectrometer 44 can be directed to a processing unit 45 for analysis and display. The integrated spectroscopy system 40 can further comprise a controller 46 that can be adapted and configured to control the light sources 42 and 43, to sequentially turn on and off the sources 42 and 43 as well as to control the output power of the light sources 42/43. Alternatively, the light sources 42/43 can be self-powered and only controlled through controller 46 using a wired interface or a wireless interface. In one implementation, the controller 46 can be adapted to control the light sources 42 and 43 so that both light sources can produce illumination light for Raman measurements and white light for reflectance measurements simultaneously. For example, the laser 42 can produce an excitation light at 785 nm and the light source 43 can produce illumination light that can be modulated so that it contains only wavelength below 750 nm so that the white light illumination light does not interfere with the excitation illumination from the laser 42.

In another implementation, the controller 46 can be adapted to control the light sources 42 and 43 so that both light sources can produce illumination light for Raman measurements and UV/visible excitation light for fluorescence measurements simultaneously. For example, the light source 43 can produce excitation light that can be modulated so that it contains only wavelength below 750 nm and its induced fluorescence light is also below 750 nm so that the excitation light produced by light source 43 does not interfere with the 785 nm excitation illumination from the laser 42.

The controller 46 can further be adapted and configured to control the detector 4 and the spectrograph 3, to turn them on and off and to read the Raman spectra data. In addition, controller 46 can control the spectrometer 44, to turn the detector of 44 on and off and to read the reflectance and fluorescence spectra data. The controller 46 can receive Raman spectra and the reflectance/fluorescence spectra from the detector 4 and spectrometer 44, respectively, and can forward the respective spectra to the processing unit 45 to further process and analyze the measured spectra and display the spectra to a monitor or any other visualization system. In addition, the controller 46 can receive signals from the light sources 42/43 and can control the operation of the spectrograph 3, detector 4, the spectrometer 44 and/or the processing unit 45. The controller 46 can be connected to a trigger button or switch 47. The switch 47 can trigger different spectral measurements, such as Raman measurements, reflectance measurement, fluorescence measurements or a combination thereof. In one implementation, the controller 46 can be configured to send a signal to an ambient light source (not shown) to automatically turn off the ambient light. For example the ambient light can be switched off for a predetermined time, e.g. one or two seconds. In one example, once the trigger switch 47 is turned on, it can send a signal to the controller 46 to switch off the ambient light. Once the detector 4 and/or spectrometer 44 detect the measured signal, it can send a signal to the controller 46 to turn on the ambient light. This can actually provide a way to tell the operator that the measurements have been completed. In one embodiment, the controller 46 can send a signal to a power system of the monitor to automatically turn off the monitor during the spectral measurements and to turn it on once the spectral measurements have been completed.

So, the integrated probe 41 can facilitates integrated measurements of Raman spectra, reflectance spectra, and fluorescence spectra. The three spectral measurements can be performed sequentially and can be completed within one to two seconds. In one implementation, as described above, the Raman and the reflectance spectral measurements can be performed simultaneously to further shorten the total tri-modality measurement time. In another implementation, the UV/Visible light excited fluorescence measurements can be configured in such a way so that the fluorescence light wavelength is below 750 nm so that it does not interfere with 785 nm excited Raman measurements and thus the UV/Visible fluorescence measurements can be performed simultaneously with the Raman measurements.

The 785 nm excitation light for Raman measurements can also induce NIR fluorescence, so the NIR fluorescence measurements and the Raman measurements can be performed simultaneously as well. So the integrated spectroscopy system 40 can provide four types of spectral information such as, Raman measurements, NIR fluorescence measurements, reflectance measurements and UV/Visible excited fluorescence measurements.

Figure 5:
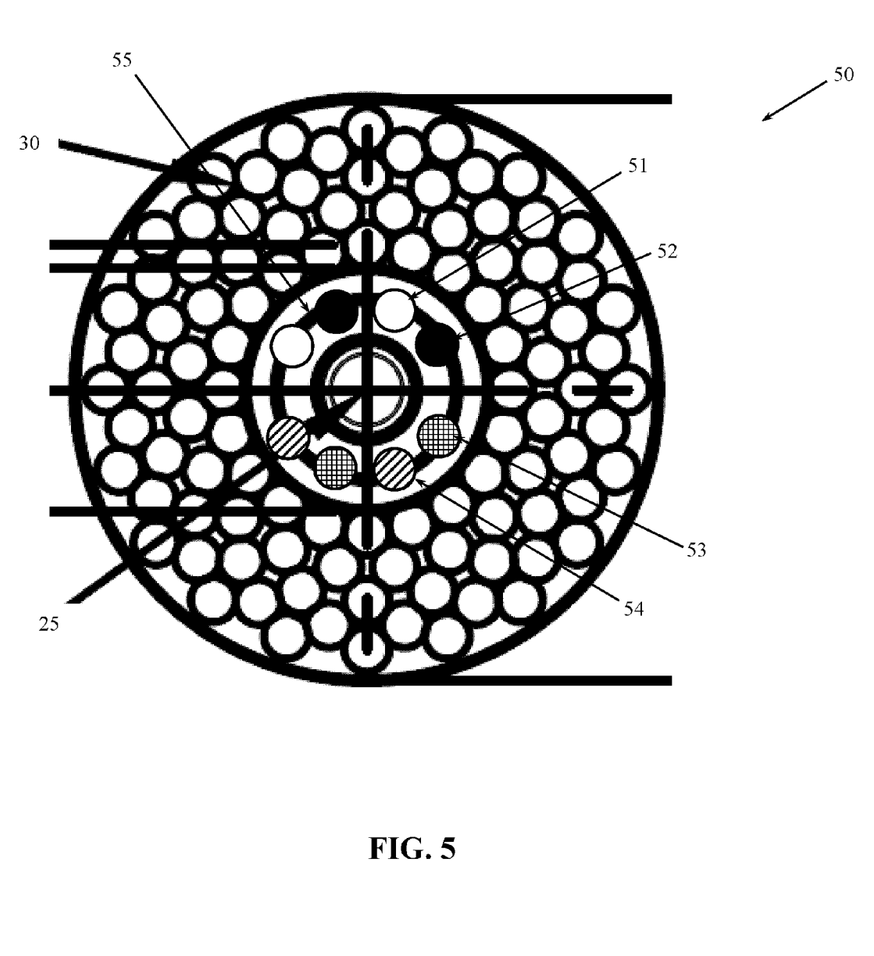
FIG. 5 is a top view of a distal end of an integrated spectral probe showing a probing fiber bundle assembly.

FIG. 5 is a top view of a distal end of the probe 41 showing a probing fiber bundle assembly 50 configured to provide an illumination light to the target and collect the returning radiation reflected, scattered or emitted from the target. The probing fiber bundle assembly 50 can be configured to accommodate an excitation illumination fiber 25 for inducing Raman/NIR fluorescence measurements, a plurality of collection fibers 30 for collecting the reflected/scattered Raman signals and/or emitted NIR fluorescence signals. The fiber bundle 50 further accommodates one or more reflectance (white light) illumination fibers 51, one or more fluorescence excitation fibers 52, one or more reflectance collection fibers 53 and one or more fluorescence collection fibers 54. At the example illustrated in the FIG. 5, the illumination fiber 25 can be located at a center of the bundle assembly 50. For example, the illumination fiber 25 can be a single 200 μm illumination fiber. In addition, the one or more reflectance (white light) illumination fibers 51, the one or more fluorescence excitation fibers 52, the one or more reflectance collection fibers 53 and the one or more fluorescence collection fibers 54 can be located centrally in a core 55 of the probing fiber bundle assembly 50 surrounding the excitation illumination fiber 25. The collection fibers 30 can be packed around the core 55 to form a round bundle. The collection fibers bundle can comprise about fifty to hundred fifty collection fibers 30 of 100 μm core diameter. For illustration purposes only, the fibers 25, 30, 51, 52, 53 and 54 can be low-OH fused silica type with numerical aperture of about 0.22. The reflectance illumination/collection fibers 51/53 and the fluorescence excitation/collection fibers 52/54 can be placed between in an annular space between the Raman excitation fiber 25 and the Raman collection fibers 30. The reflectance collection fibers 53 and fluorescence collection fibers 54 can comprise about 1 to 6 collection fibers of 100 μm core diameter. There can be no filters over the reflectance illumination/collection fibers 51/53 and/or fluorescence excitation/collection fibers 52/54 except an anti-reflection coating. In one embodiment a filter can be placed over the illuminations fibers 51 and 52 to block the light above 750 nm to prevent any interference with the Raman illumination light. In one implementation, a space can be provided between the Raman excitation fiber 25 and the Raman collection fibers 30 as well as between the reflectance illumination fibers 51 and the reflectance collection fibers 53, and between the fluorescence excitation fibers 52 and the fluorescence collection fibers 54 to prevent any cross-talking and interference between the respective tissue signals. Filters, such as long-pass filters 23b and/or short pass filter 23a can be coated over the collection fibers 30 and/or excitation illumination fiber 25 as described herein above. In one implementation, filters 23a and 23b can be coated on a substrate glass and be aligned and glued to the end of the fiber bundle assembly 50 as described herein above. In addition filters blocking light above 750 nm can be placed over illumination fibers 51 and 52 to prevent interference with the Raman illumination light. In one implementation, a distal tip of the probe 41 can be disposable to prevent cross-contamination between patients.

Figure 6:
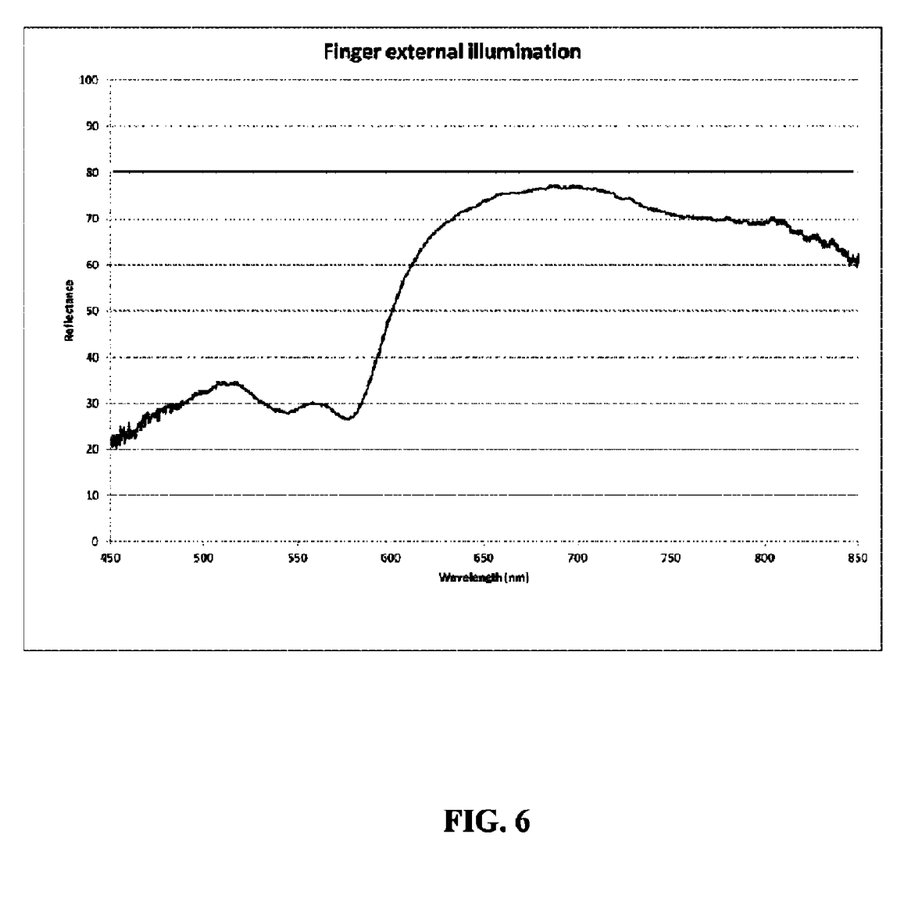
FIG. 6 is a graphical illustration of an example of a reflectance spectrum of a skin tissue obtained with an integrated spectral probe.
Figure 7:
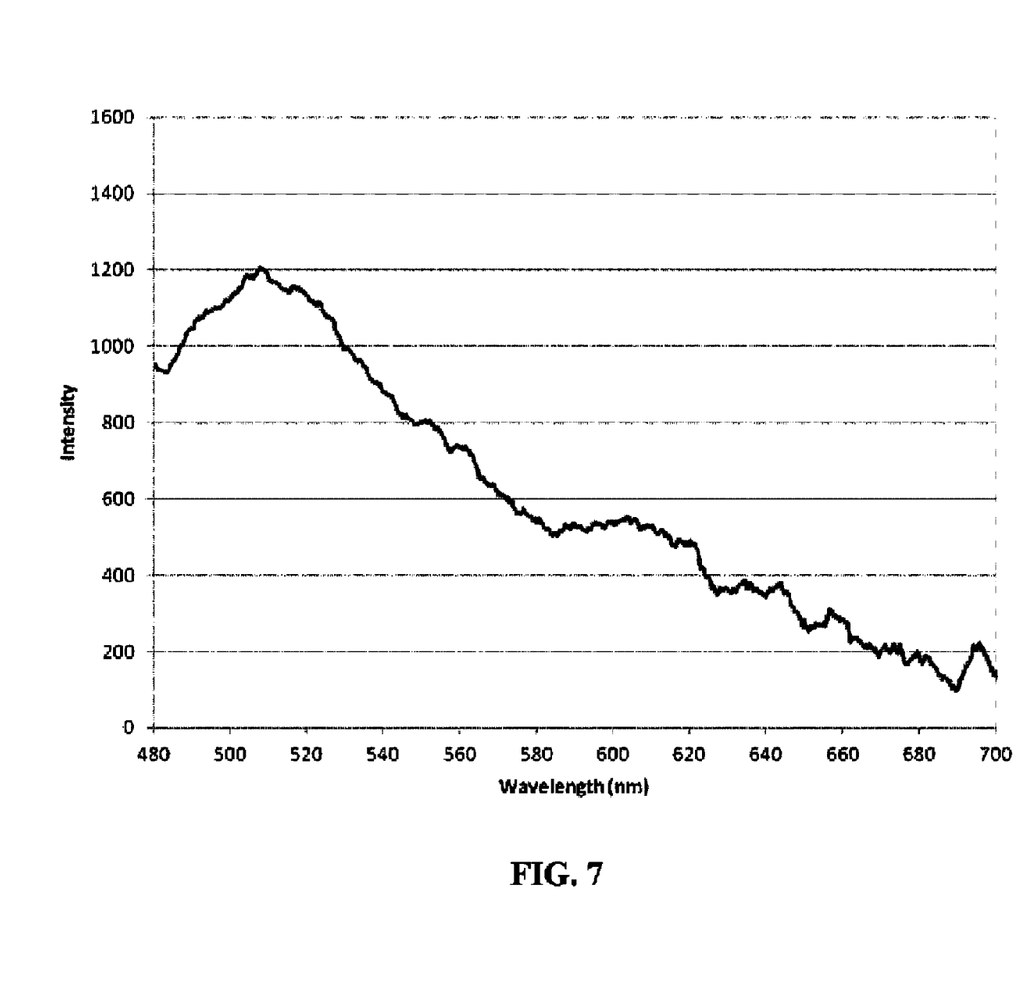
FIG. 7 is a graphical illustration of an example of a fluorescence spectrum of a skin tissue obtained with an integrated spectral probe.

FIGS. 6 and 7 graphically illustrate an example of a reflectance spectrum of a skin tissue obtained with the integrated spectral probe 41 (FIG. 6) and an example of a fluorescence spectrum of a skin tissue (FIG. 7).

While particular elements, embodiments and applications of the present disclosure have been shown and described, it will be understood, that the scope of the disclosure is not limited thereto, since modifications can be made without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and subcombinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments. Indeed, the novel methods and systems described herein may be embodied in a variety of other forms; furthermore, various omissions, additions, substitutions, equivalents, rearrangements, and changes in the form of the embodiments described herein may be made without departing from the spirit of the inventions described herein.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

The example calculations, simulations, results, graphs, values, and parameters of the embodiments described herein are intended to illustrate and not to limit the disclosed embodiments. Other embodiments can be configured and/or operated differently than the illustrative examples described herein. Indeed, the novel methods and apparatus described herein may be embodied in a variety of other forms; furthermore, various omissions, substitutions and changes in the form of the methods and systems described herein may be made without departing from the spirit of the inventions disclosed herein.

The invention claimed is:

1. An integrated spectroscopy system to facilitate integrated measurements of Raman spectra, reflectance spectra and fluorescence spectra, the system comprising:
a light source configured to provide a white light illumination beam to generate reflectance spectra, an excitation light beam to generate an UV/visible fluorescence spectra and a narrow band excitation light beam to induce Raman spectra;
an integrated spectroscopy probe coupled to the light source, the spectroscopy probe comprising:
at least one narrow band excitation fiber configured to transmit the narrow band excitation light beam to a target;
at least one white light illumination fiber configured to transmit the white light illumination beam to the target;
at least one excitation illumination fiber configured to transmit the excitation light beam to the target;
a plurality of Raman collection fibers configured to collect a returning radiation reflected and emitted from the target in response to the narrow band excitation light beam;
at least one reflectance collection fiber configured to collect a returning radiation reflected from the target in response to the white light illumination beam; and
at least one fluorescence collection fiber configured to collect returned radiation emitted from the target in response to the excitation light beam;
a first detector coupled to the plurality of Raman collection fibers to detect a Raman spectrum; and
at least one additional detector coupled to the at least one reflectance collection fibers and/or the at least one fluorescence collection fibers to detect a reflectance spectrum and/or a fluorescence spectrum,
wherein the at least one white light illumination fiber, the at least one excitation illumination fiber, the at least one reflectance collection fiber and the at least one fluorescence collection fiber are placed between the at least one narrow band excitation fiber and the plurality of Raman collection fibers and are each spaced apart from the at least one narrow band excitation fiber and the plurality of Raman collection fibers.

2. The integrated spectroscopy system of claim 1, wherein pluralities of spectral measurements are being performed within 2 seconds or less.

3. The integrated spectroscopy system of claim 1, further comprise an optical modulator mounted in front of the light source configured to modulate the illumination light from the light source and provide the white light illumination light beam, the excitation light beam and the narrow band excitation beam.

4. The integrated spectroscopy system of claim 3, wherein the optical modulator comprises a first filter configured to pass visible light below 750 nm, a second filter configured to pass excitation light in a blue wavelength range and a third filter configured to pass light in a 785±5 nm wavelength range.

5. The integrated spectroscopy system of claim 1, wherein the light source comprises a monochromatic light source configured to provide the narrow band excitation light beam, a broadband light source configured to provide white light illumination light beam and a excitation light source configured to provide the excitation light beam, the monochromatic light source being coupled to the at least one narrow band excitation fiber, the broadband light source being coupled to the at least one white light illumination fiber, the excitation light source being coupled to the at least one excitation illumination fiber.

6. The integrated spectroscopy system of claim 5, wherein the broadband light source and the excitation light source are integrated into one light source, the integrated light source is configured to provide a white light illumination light beam and the excitation light beam in sequence.

7. The integrated spectroscopy system of claim 1, wherein the at least one narrow band excitation fiber is spaced apart from the plurality of Raman collection fibers; the at least one white light illumination fiber is spaced apart from the at least one reflectance collection fiber; and the at least one excitation illumination fiber is spaced apart from the at least one fluorescence collection fiber.

8. The integrated spectroscopy system of claim 1, further comprises a filter assembly mounted at a distal end of the spectroscopy probe, the filter assembly comprising a short pass filter placed over the at least one narrow band excitation fiber to pass light in a 785±5 nm wavelength range and a long pass filter placed over the plurality of Raman collection fibers to block light in a 785 nm wavelength range and pass light in a wavelength range above 800 nm.

9. The integrated spectroscopy system of claim 8, wherein the filter assembly being glued to the distal end of the probe, the probe further comprising a grooved channel formed at the distal end configured to capture any excess glue.

10. The integrated spectroscopy system of claim 1, wherein the probe further comprises a filter mounted into the probe at a proximal end of the probe, the filter being coupled to the at least one narrow band excitation fiber to pass light in a 785±5 nm wavelength range.

11. The integrated spectroscopy system of claim 1, wherein the at least one additional detector is a compact spectrometer.

12. The integrated spectroscopy system of claim 1, further comprising a control system in optical communication with the light source to control the output illumination of the light source.

13. The integrated spectroscopy system of claim 12, wherein the control system being in optical communication with the first detector and the at least one additional detector, the control system configured to control the operation of the first detector and the at least one additional detector.

14. The integrated spectroscopy system as in one of claims 1-13, wherein the light source provides simultaneously the white light illumination beam and the narrow band excitation beam such that the first detector and the one additional detector provide simultaneously the Raman spectrum and the reflectance spectrum.

15. The integrated spectroscopy system as in one of claims 1 to 13, wherein the light source provides simultaneously the excitation light beam and the narrow band excitation light beam such that the first detector and the one additional detector provide simultaneously the Raman spectrum and the fluorescence spectrum.

16. The integrated spectroscopy spectrum as in one of claims 1 to 13, wherein the light source is configured to provide the narrow band illumination light beam to generate simultaneously a Raman spectrum and an infrared fluorescence spectrum such that the first detector being configured to provide simultaneously the Raman spectrum and the infrared fluorescence spectrum.

\* \* \* \* \*